(12) United States Patent
Jiang et al.

(10) Patent No.: US 9,566,392 B2
(45) Date of Patent: Feb. 14, 2017

(54) NEEDLE-EXCHANGEABLE AND SELF-DESTRUCTION INSULIN SYRINGE

(75) Inventors: Xiaohui Jiang, Wenling (CN); Zuoqian Lin, Wenling (CN)

(73) Assignee: Sol-Millennium Medical HK Limited, Hong Kong (CN)

( * ) Notice: Subject to any disclaimer, the term of this patent is extended or adjusted under 35 U.S.C. 154(b) by 174 days.

(21) Appl. No.: 13/806,647

(22) PCT Filed: Oct. 19, 2010

(86) PCT No.: PCT/CN2010/077861
§ 371 (c)(1),
(2), (4) Date: Sep. 10, 2013

(87) PCT Pub. No.: WO2011/160364
PCT Pub. Date: Dec. 29, 2011

(65) Prior Publication Data
US 2013/0345630 A1     Dec. 26, 2013

(30) Foreign Application Priority Data
Jun. 21, 2010   (CN) .......................... 2010 1 0204868

(51) Int. Cl.
*A61M 5/32*       (2006.01)

(52) U.S. Cl.
CPC ........ *A61M 5/322* (2013.01); *A61M 2005/323* (2013.01)

(58) Field of Classification Search
CPC .. A61M 5/178; A61M 5/315; A61M 5/31501; A61M 5/31505; A61M 5/50; A61M 5/5013; A61M 5/502; A61M 2005/5026; A61M 2005/5033; A61M 5/348; A61M 5/322; A61M 2005/323; A61M 2005/31521; A61M 5/31511
(Continued)

(56) References Cited

U.S. PATENT DOCUMENTS 5,807,323 A * 9/1998 Kriesel ............. A61M 5/14526
                                                604/232
2008/0275394 A1* 11/2008 Luo et al. ..................... 604/110
2010/0030146 A1*  2/2010 Kakish et al. ................ 604/110

FOREIGN PATENT DOCUMENTS

CA    2724997      * 11/2009 ............. A61M 5/50
CN    2782120 Y      5/2006
(Continued)

OTHER PUBLICATIONS

Australian Government, IP Australian, Patent Examination Report No. 1, Patent Application No. 2010355916, May 14, 2015, three pages.
(Continued)

*Primary Examiner* — Nathan R Price
*Assistant Examiner* — Melissa A Snyder
(74) *Attorney, Agent, or Firm* — Fenwick & West LLP

(57) ABSTRACT

A needle-exchangeable and self-destruction insulin syringe comprises a barrel (1), a push rod (2), a rubber piston (3) and a needle seat (4). The barrel (1) is provided with a connection needle seat (7) matched with a needle hub (5). The connection needle seat (7) is supported and fastened at the front end of the barrel by a support seat (8). The needle hub (5) is extended downwards to form a fixing ring (9). A snap ring (10) is formed at an upper end of the connection needle seat (7). The snap ring (10) is protruded into the bore of the fixing ring (9) and locked with the fixing ring (9). A large groove (13) is provided in the wall of the bore of the connection needle seat (7). The upper end of the support seat (8) is protruded into the bore of the connection needle seat (7). First elastic detents (14) are formed at the upper end of the support seat (8) and come together towards the center. A ring of flange (15) is provided at the outside of the upper end of the support seat, and falls in the large groove (13), capable of sliding up and down along the large groove (13). First
(Continued)

elastic support pawls (16) are formed at the lower end of the connection needle seat (7), and the inner wall of the barrel is correspondingly provided with a small groove (17) in which the first elastic support pawls (16) can be embedded. A ring of flange shoulder (18) is provided at the outside of the lower end of the support seat, and abuts against the first elastic support pawls (16).

2 Claims, 9 Drawing Sheets

(58) Field of Classification Search
USPC ........ 604/93.01, 110, 162, 164.08, 192, 195, 604/263
See application file for complete search history.

(56) References Cited

FOREIGN PATENT DOCUMENTS

| | | |
|---|---|---|
| CN | 2863143 Y | 1/2007 |
| CN | 2892119 Y | 4/2007 |
| CN | 100425303 C | 10/2008 |
| CN | 201194970 Y | 2/2009 |
| CN | 201324418 Y | 10/2009 |
| EP | 1 550 476 A1 | 7/2005 |
| GB | 1031950 A | 6/1966 |
| JP | H11-299890 A | 11/1999 |
| WO | WO 2006/121611 A2 | 11/2006 |
| WO | WO 2009/052642 | 4/2009 |

OTHER PUBLICATIONS

Canadian Office Action, Canadian Application No. 2,804,299, Dec. 19, 2013, three pages.
European Patent Office, European Search Report and Opinion, European Application No. 10853503.0, Dec. 2, 2013, seven pages.
PCT International Search Report and Written Opinion, PCT Application No. PCT/CN2010/077861, Mar. 31, 2011, eleven pages.
Russian Intellectual Property Office, Office Action, Russian Patent Application No. 2013101551, Feb. 25, 2014, seven pages.

* cited by examiner

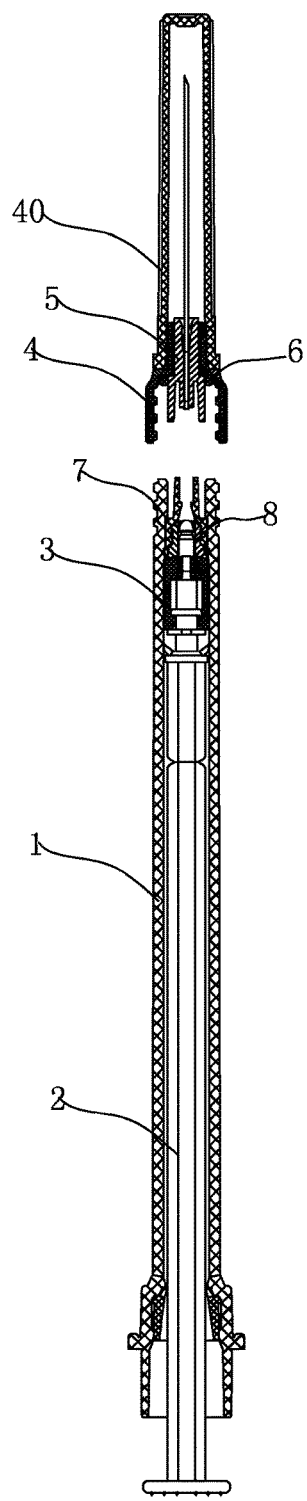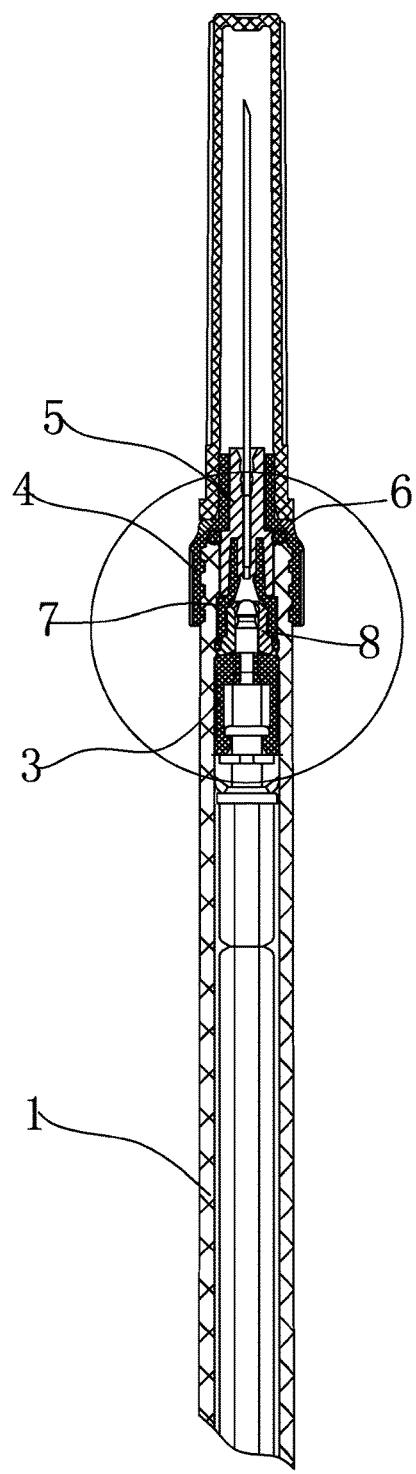
Fig. 1
Fig. 2

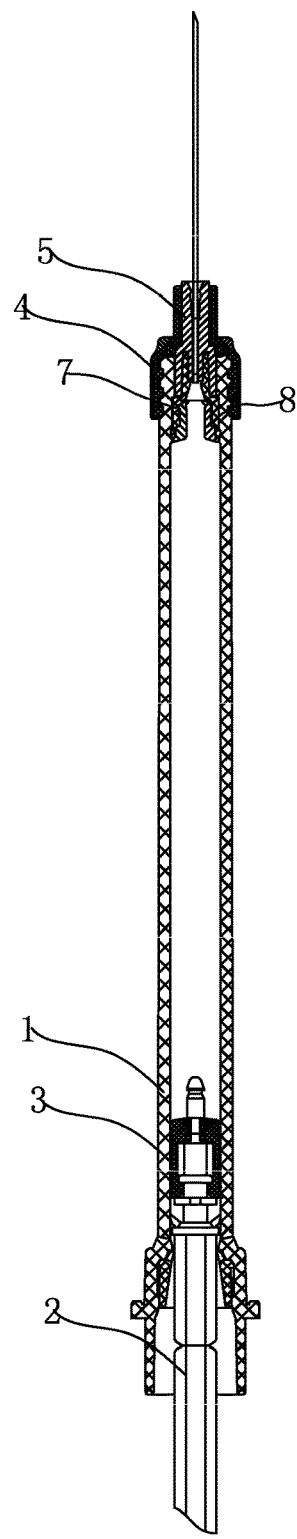
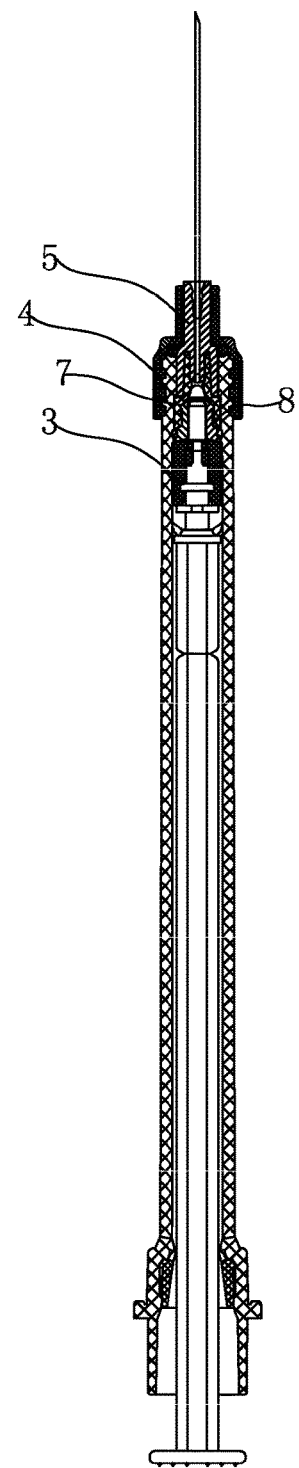
Fig. 3
Fig. 4

NEEDLE-EXCHANGEABLE AND SELF-DESTRUCTION INSULIN SYRINGE

FIELD OF THE INVENTION

The present invention relates to a medical instrument, and particularly to a disposable needle-exchangeable and self-destroying insulin syringe.

BACKGROUND OF THE INVENTION

As people's living standard is improved, a rate of incidence of diabetes is gradually increasing. According to statistics, at present there are approximately 40 million diabetes patients in China. Studies show that injection of insulin at an early stage assists in protecting the function of a patient's islet β cells and preventing occurrence of complications. Therefore, the most important measure for treating diabetes is to inject insulin. The conventional insulin syringes are usually confronted with the problem of reusability and a high scrappage during manufacture. Currently, there are some self-lock insulin syringes available in the market in which during injection, a force for pushing the piston is not consistent, and when a liquid medicament is right injected up, the pushing force must be increased a little so that an instant speed of the liquid medicament entering the patient's body is quickened, thereby causing pains to the patient. There are also some self-destroying insulin syringes in which an aperture is formed through the rubber piston after use. Also, some syringes, which are provided with safety devices to avoid a needle from pricking a patient's body due to exposure during operation, by no means achieves an object of self-destruction. Since a barrel of an insulin syringe has a smaller inner diameter, it is not easy to place a reasonable self-destroying mechanism in the barrel with such smaller inner diameter. Besides, the needles of the conventional insulin syringes are mostly fixed together with the barrel so that needles of different specifications cannot be changed as desired to meet different needs of the broad mass of patients. Up to now, in the market there is not yet developed a self-destroying insulin syringe in which needles of different specifications can be changed as desired and the needles can be retracted into the barrel upon completion of injection.

SUMMARY OF THE INVENTION

The technical problem to be solved by the present invention is to provide an insulin syringe in which the needles of different specifications can be changed as desired and the needles can be refracted into a barrel upon completion of injection.

In order to solve the above technical problem, the present invention employs the following technical solution:

A needle-replaceable and self-destroying insulin syringe comprises a barrel, a push rod, a rubber piston and a needle seat, a front end of the push rod being connected to a conical boss via a snap core, the needle seat being detachably connected to a front end of the barrel, a needle hub for mounting the needle being provided in the needle seat, a water-tight elastic O-sealing ring being provided between the needle hub and the needle seat, characterized in that the barrel is provided with a connection needle seat cooperating with the needle hub, the connection needle seat is supported and fixed at the front end of the barrel by a support seat, the needle hub extends downwards to form a fixing ring, a snap ring is formed at an upper end of the connection needle seat, the snap ring protrudes into a bore of the fixing ring and is snap-fitted with the fixing ring, a large groove is provided in a wall of the bore of the connection needle seat, an upper end of the support seat protrudes into the bore of the connection needle seat, first elastic detents are formed at the upper end of the support seat and come together towards the center, a ring of flange is provided at the outside of the upper end of the support seat and seats in the large groove, capable of sliding up and down along the large groove, first elastic support pawls are formed at a lower end of the connection needle seat, and the inner wall of the barrel is correspondingly provided with a small groove in which the first elastic support pawls can be embedded, a ring of flange shoulder is provided at the outside of the lower end of the support seat, and abuts against the first elastic support pawls.

The needle hub is formed with a circular flange in the fixing ring, when the snap ring is assembled with the fixing ring, the bore of the snap ring inwardly presses the circular flange to maintain liquid sealing therebetween and prevent liquid leakage.

An inner wall of the fixing ring is in a taper fit with an outer wall of the snap ring.

The rubber piston is hollow, and the push rod is provided with a conical surface supporting a bore of the rubber piston and a stop piece abutting against the rubber piston.

The needle seat is threadedly connected to the front end of the barrel, a stop flange is provided on a wall of a bore of the needle seat to limit position with respect to the front end of the barrel.

The stop piece is in a cross shape or multi-rib shape.

In such syringe with the above structure is, since the needle hub is detachably connected to the barrel, needles of different specifications can be replaced as needed, and meanwhile, the needle hub can be retracted into the barrel on completion of the injection. Since the inner wall of the fixing ring is taper-fitted with the outer wall of the snap ring, liquid sealing therebetween can be maintained and liquid leakage can be prevented. The stop piece on the push rod is designed in a cross shape or a multi-rib shape, thereby effectively reducing a compression force from the stop piece to the rubber piston, and preventing the rubber piston from serious deformation due to compression.

BRIEF DESCRIPTION OF DRAWINGS

FIG. 1 is a structural schematic view of the present utility model;

FIG. 2 is a cross-sectional view of a syringe in a non-use state;

FIG. 3 is a cross-sectional view of a liquid-drawn state;

FIG. 4 is a cross-sectional view showing a state upon completion of injection;

DETAILED DESCRIPTION OF PREFERRED EMBODIMENTS

Figure 5:
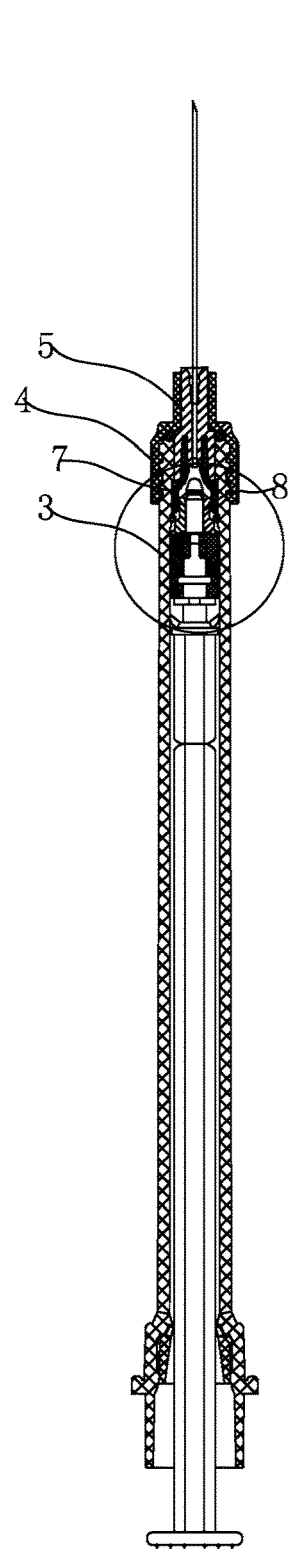
FIG. 5 is a cross-sectional view showing a state that a needle begins to be retracted.

Referring to FIG. 1 and FIG. 2, the present invention comprises a hollow barrel 1, a push rod 2 slideable in the barrel, a rubber piston 3 mounted at a front end of the push rod, and a needle seat 4 mounted at a front end of the barrel 1. The needle seat 4 is detachably connected to the front end of the barrel. The detachable connection in the embodiment employs a threaded connection. Certainly, other connecting modes such as snap-fitting can also be employed. A sheath 40 is mounted on an outer circumference of a head portion of the needle seat 4 to prevent the needle from collision, and from hurting a patient. The sheath covers again the head portion of the needle seat on completion of injection, and residual liquid will not leak.

Figure 11:
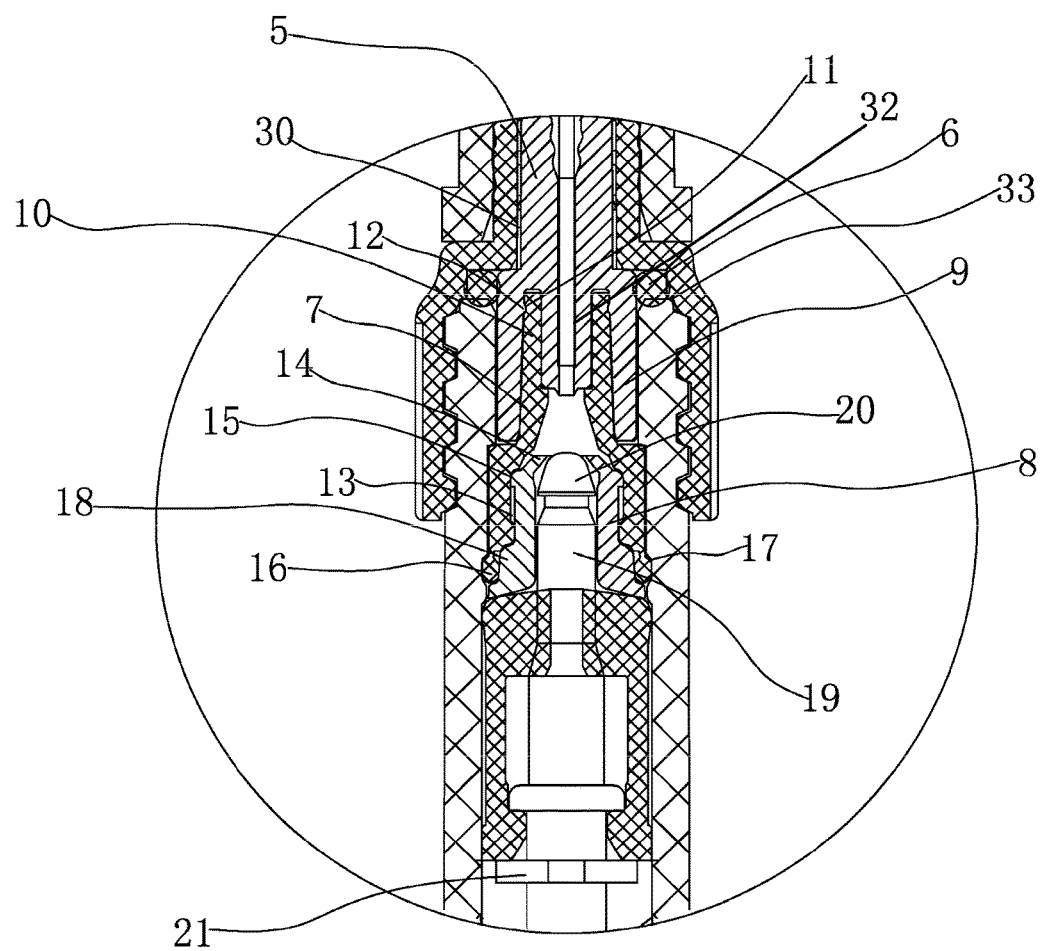
FIG. 11 is a partial enlarged view of FIG. 2.
Figure 14:
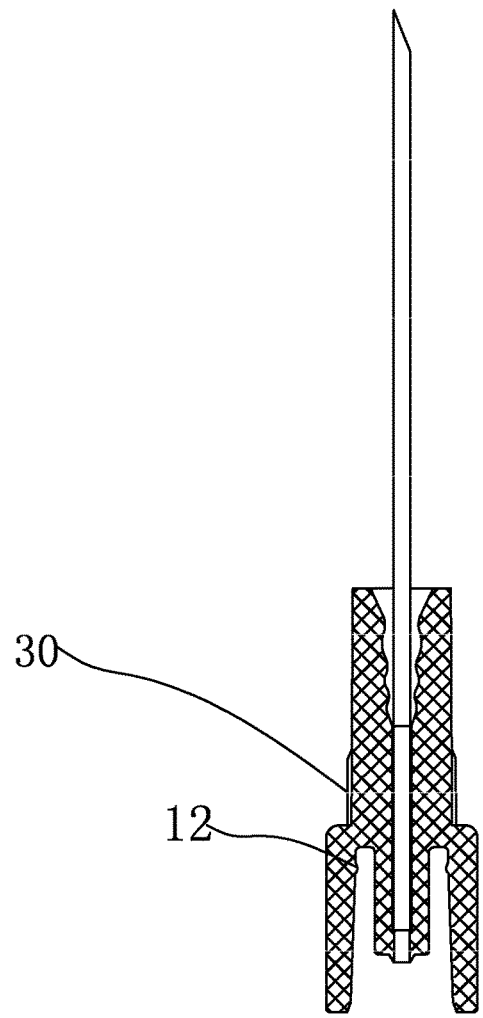
FIG. 14 is a structural schematic view of a needle hub.
Figure 15:
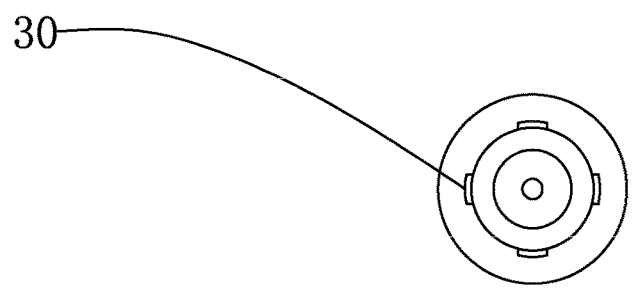
FIG. 15 is a top view of the needle hub.

Referring to FIG. 11, a stop flange 33 is provided on a wall of a bore of the needle seat 4 to limit position with respect to the front end of the barrel. A needle hub 5 for mounting the needle is provided in the needle seat 4 A water-tight elastic O-sealing ring 6 is provided between the needle hub 5 and the needle seat 4 to prevent injecta from leaking outside the barrel. At least three reinforcing ribs 30 are provided axially along the circumference of the needle hub 5 (see FIGS. 14 and 15). The reinforcing ribs 30 cooperate with an inner circumference of the needle seat 4 to play a role of fixing the needle seat 4. The needle hub 5 extends downwards to form a fixing ring 9. The needle hub 5 is formed with a circular boss 32 in the fixing ring 9, the circular boss 32 is provided with a needle hole. The circular boss 32 ensures none generation of air bubble during injection and ensures firmness and verticality of the needle glue drop process. In the barrel is provided with a connection needle seat 7 cooperating with the needle hub 5. The connection needle seat 7 is provided with a bore for passage of the injecta. The connection needle seat 7 is supported and fixed at a front end of the barrel by a support seat 8. A snap ring 10 is formed at an upper end of the connection needle seat 7. The snap ring 10 protrudes into a bore of the fixing ring 9 and is snap-fitted and fixed with the fixing ring 9. An inner wall of the fixing ring 9 is in a tape-fit with an outer wall of the snap ring 10. When the snap ring 10 is assembled with the fixing ring 9, the bore of the snap ring inwardly presses the circular boss 32 to maintain liquid sealing therebetween and prevent liquid leakage. A snap slot 11 is provided at the outside of the upper end of the snap ring 10, and a projection 12 corresponding to the snap slot 11 is provided on a wall of the bore of the fixing ring (see FIG. 14). A large groove 13 is provided in a wall of the bore of the connection needle seat 7. An upper end of the support seat 8 protrudes into the bore of the connection needle seat 7 and is provided with first elastic detents 14 coming together towards the center. A ring of flange 15 is provided at the outside of the upper end of the support seat 8, and seats in the large groove 13, capable of sliding up and down along the large groove 13. First elastic support pawls 16 are formed at a lower end of the connection needle seat 7. There are at least two first elastic support pawls 16. The inner wall of the barrel is correspondingly provided with a small groove 17 in which the first elastic support pawls can be embedded. A ring of flange shoulder 18 is provided at the outside of the lower end of the support seat 8, and abuts against the first elastic support pawls 16 so that the first elastic support pawls 16 seat into the small groove 17 to fix the lower end of the connection needle seat. The support seat 8 and the connection needle seat 7 and the inner wall of the barrel abut against one another to be fixed at the front end of the barrel.

Figure 10A:
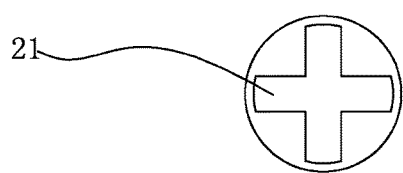
FIG. 10a-FIG. 10c show cross-sectional views taken along A-A of FIG. 9.
Figure 10B:
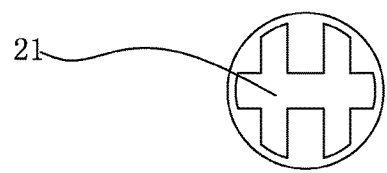
Figure 10C:
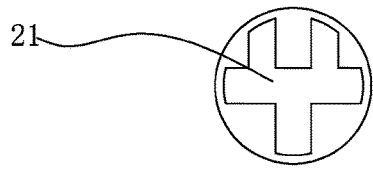
Figure 9:
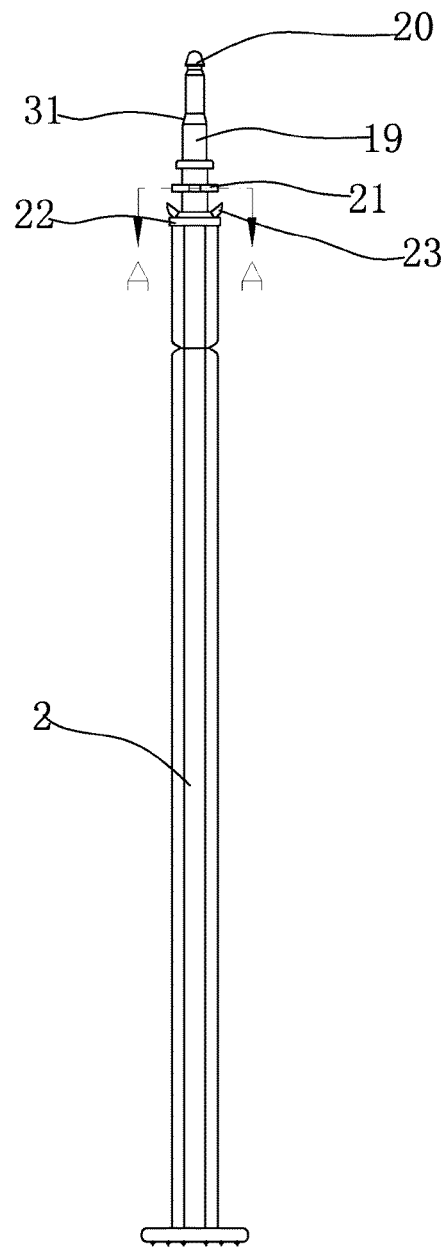
FIG. 9 is a structural schematic view of a push rod.

Referring to FIG. 9, the push rod 2 is provided a conical surface 31 supporting a bore of the rubber piston 3. When the liquid is pushed, the rubber piston deforms due to compression of the injecta to move the push rod 2 forwardly, the conical surface 31 supports the bore of the rubber piston to produce an abutting force to ensure a positive pressure and no leakage. The front end of the push rod 2 is connected to a conical boss 20 via a snap core 19. On completion of the injection, the conical boss 20 is snap-fitted with the first elastic detent 14. The rubber piston 3 is hollow. The push rod 2 is provided with a stop piece 21 abutting against a bottom surface of the rubber piston 3. At the same time, the stop piece 21 functions to fix the rubber piston 3. Before the liquid is drawn, the front end of the rubber piston abuts against 0-level line to allow for a standard volume of liquid or blood drawn and refrain from air exhaust trouble. Upon injection, the rubber piston deforms due to compression from a counter-action generated by the injecta and a push force of the stop piece 21, and the conical boss 20 at the front end of the push rod extends forwardly in an axial direction of the push rod. Upon completion of injection, the conical boss 20 can be snap-fitted with the first elastic detent 14. In order to reduce the compression exerted by the stop piece 12 to the rubber piston to avoid the rubber piston from serious deformation due to compression, the stop piece 21 is in a cross shape or multi-rib shape (see FIG. 10a-FIG. 10c). The cross-shaped or multi-rib-shaped stop piece can reduce a contact area with the rubber piston (as compared with the circular platform shape), whereby achieving the purpose of reducing the compression force.

Figure 12:
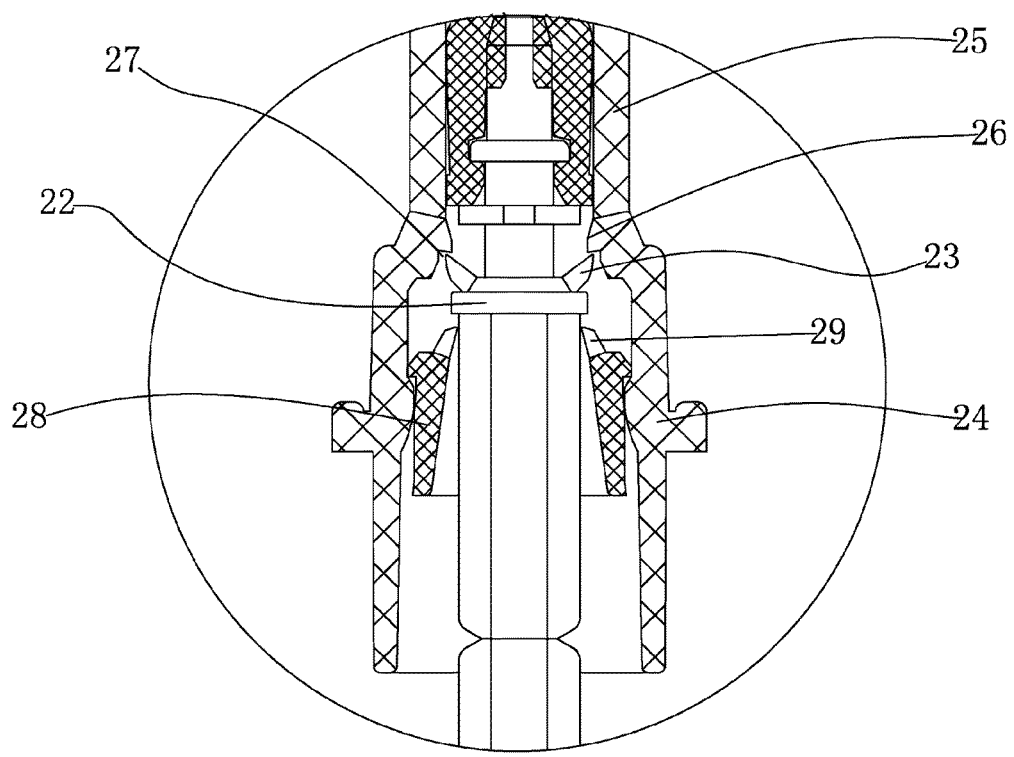
FIG. 12 is a partial enlarged view of FIG. 7.

Referring to FIG. 12, the push rod 2 is provided with a circular flange 22 below the rubber piston 3. The circular flange 22 is provided with second elastic detents 23 extending angularly towards the inner wall of the barrel. At a distal end of the barrel is provided a diameter enlarged portion 24. A sloped step 26 is provided at a transition between a diameter non-enlarged portion 25 and the diameter enlarged portion 24 of the barrel. Below the sloped step 26 is provided a recess 27 in which the second elastic detent 23 can be snap-fitted when the push rod is pulled downwardly. In the diameter enlarged portion 24 is provided a stop ring 28 which can abut against a bottom portion of the circular flange 22. At an upper end of the stop ring 28 are provided second elastic support pawls 29 which come together towards the center and can abut against a bottom portion of the circular flange 22. The tips of the second elastic detents 23 rise angularly upwardly towards the front end of the barrel. The stop ring 28 movably fits with an inner wall of the diameter enlarged portion 24 at the distal end of the barrel and can move up and down in an axial direction. The upper end of the stop ring 28 can abut against the bottom portion of the circular flange 22. Upon completion of the injection, the push rod 2 is pulled to move towards the bottom portion of the barrel, the bottom plane of the circular flange 22 on the push rod 2 touches tips of second elastic support pawls 29 of the stop ring 28 mounted in the barrel 1 so as to bring the stop ring 28 to move downwardly. The push rod 2 continues to be pulled downwardly, the second elastic detents 23, after passing the sloped stop 26, restore to their original natural states by virtue of their respective elasticity. The tips of the second elastic detents 23 will be snap-fitted into recesses 27 below the sloped steps 26, achieving the purpose of locking the push rod.

Figure 6:
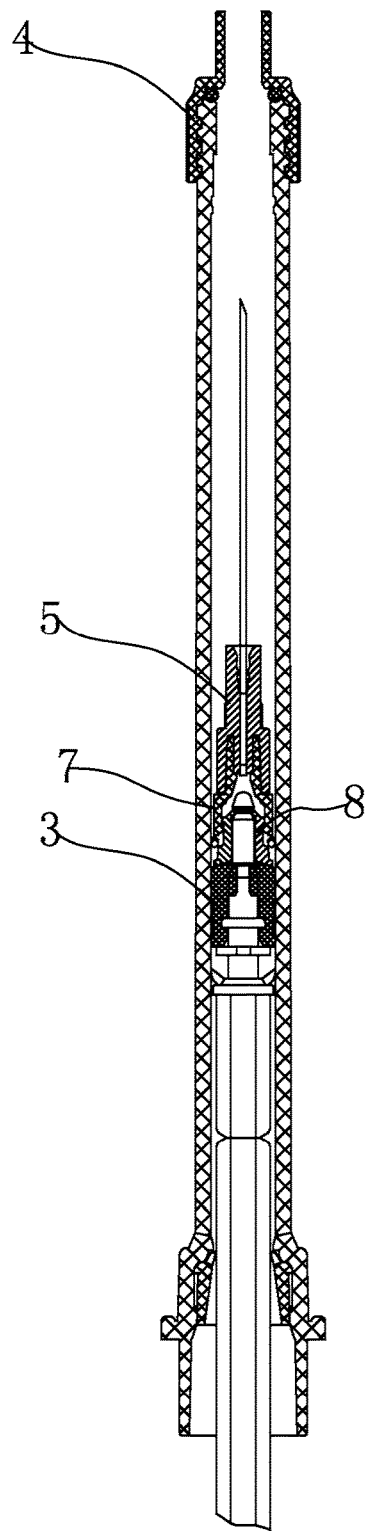
FIG. 6 is a cross-sectional view showing a state in which the needle is retracted into a barrel.
Figure 7:
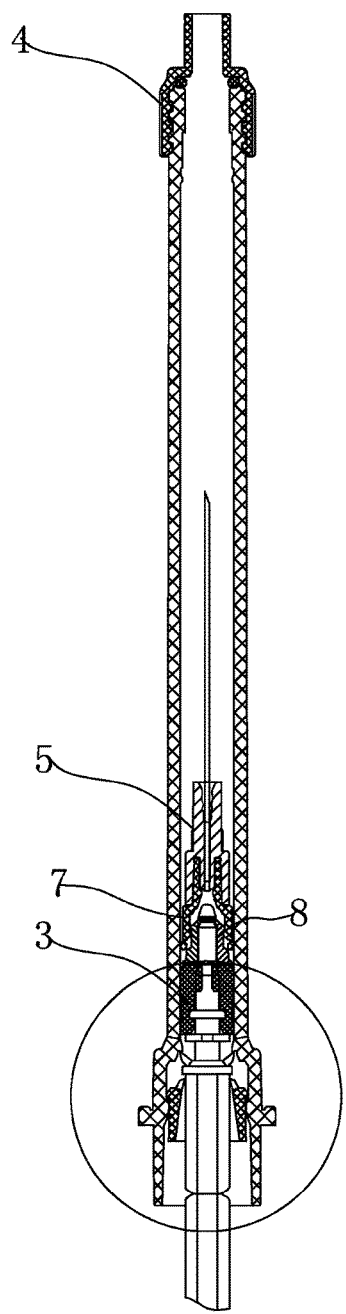
FIG. 7 is a cross-sectional view showing a state in which a push rod is locked.
Figure 8:
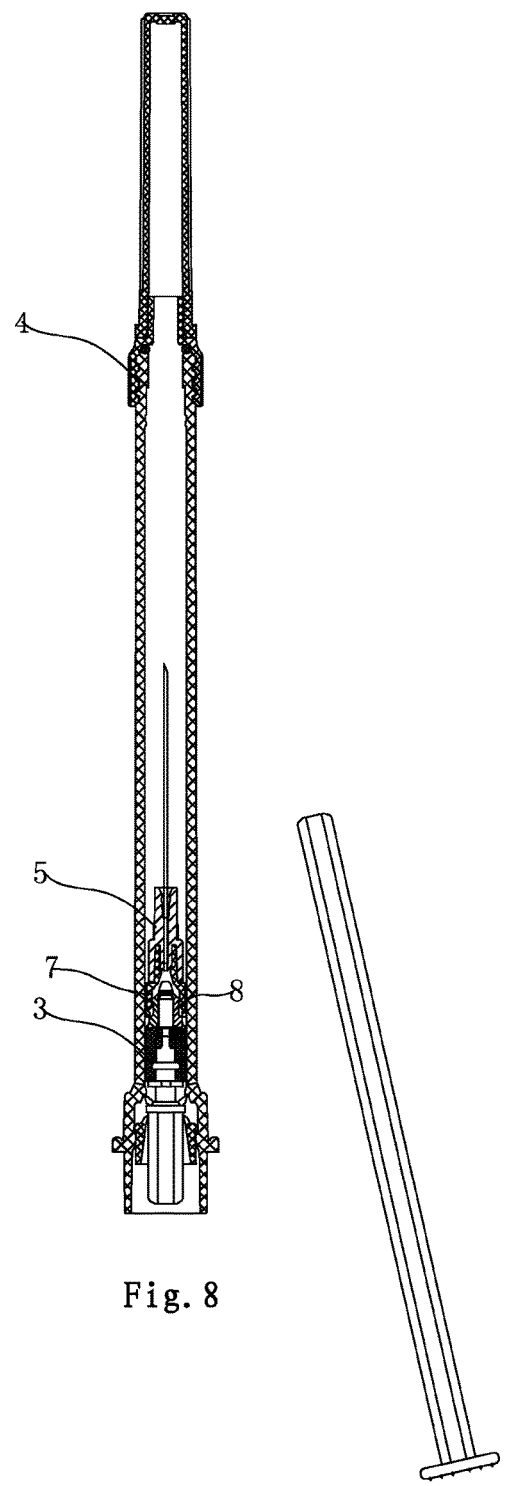
FIG. 8 is a schematic view showing a state upon completion of self-destruction.
Figure 13:
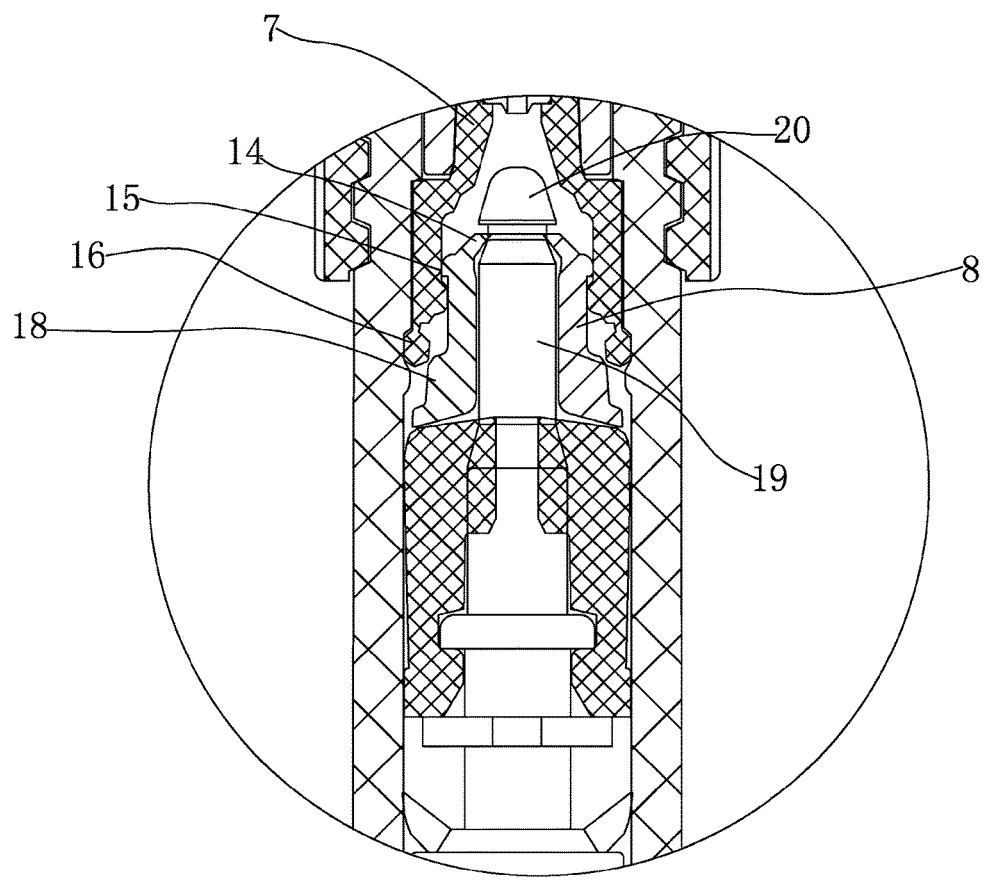
FIG. 13 is a partial enlarged view of FIG. 5.

In use of the present invention, first, as shown in FIG. 2 showing a state in which the push rod 2 is mounted in the barrel, the rubber piston 3 is already pushed to the bottom, the conical boss 20 does not pass through the first elastic detents 14 yet. As shown in FIG. 3, a liquid-drawing state is illustrated. As shown in FIG. 4, on completion of injection, the push rod 2 is further pushed forwardly due to inertia of the pushing force, and the stop piece 21 compresses the rubber piston in the axial direction of the push rod so that the conical boss 20 at the front end of the push rod extends forwardly and is snap-fitted with the first elastic detents 14. As shown in FIG. 5, the push rod is pulled downwardly, the conical boss 20 abuts against the first elastic detents 14 on the support seat and brings the support seat 8 to slide downwardly so that the first elastic support pawls 16 on the connection needle seat separate from the inner wall of the barrel, and the support seat 8 is limited by the flange 15 at the outside cooperating with a lower step of the large groove 13 of the connection needle seat (see FIG. 13). As shown in FIG. 6, the push rod is further pulled downwardly, the support seat 8 brings the connection needle seat 7 into motion, the connection needle seat 7 in turn brings the needle hub 5 to slide downwardly to retract the needle in the barrel. As shown in FIG. 7, the push rod is further pulled downwardly, the second elastic detents 23 slide downwardly along the sloped step 26, and are snap-fitted into the recesses below the sloped steps 26 (see FIG. 12), and the push rod 2 is locked. As shown in FIG. 8, the push pod is broken with a force to finish self destruction, and the needle hub is immediately covered by the sheath 40 to prevent residual liquid leakage.

What is claimed is:

1. A needle-replaceable and self-destroying insulin syringe, comprising a barrel, a push rod, a rubber piston and a needle seat, the push rod having a front end being connected with a conical boss via a snap core, the needle seat being detachably connected to a front end of the barrel and being provided therein with a needle hub for mounting a needle, a water-tight elastic O-sealing ring provided between the needle hub and the needle seat and to contact an outer surface of the barrel, characterized in that the needle hub extends downwards to form a fixing ring and is formed with a circular boss in the fixing ring;

the circular boss is provided with a needle hole, the needle hole adapted to hold a needle;

a connection needle seat is provided in the barrel for cooperating with the needle hub, wherein the connection needle seat is provided with a bore for passage of injecta, and is supported and fixed at the front end of the barrel by a support seat;

a snap ring is formed at an upper end of the connection needle seat, protrudes into a bore of the fixing ring and is snap-fitted and fixed with the fixing ring, wherein an inner wall of the fixing ring is in a taper-fit with an outer wall of the snap ring; and when the snap ring is assembled with the fixing ring, a bore of the snap ring inwardly presses the circular boss.

2. The self-destroying insulin syringe of claim 1, characterized in that the push rod further comprises a conical surface which is below the conical boss and is configured to support and liquid-tightly engage a bore of the rubber piston during injection.

* * * * *